(12) United States Patent
Zinobile et al.

(10) Patent No.: US 8,378,141 B2
(45) Date of Patent: Feb. 19, 2013

(54) PROCESS AND SYSTEM FOR SUPPLYING VAPOR FROM DRYING COLUMN TO LIGHT ENDS COLUMN

(75) Inventors: Raymond J. Zinobile, Houston, TX (US); Ronald David Shaver, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 269 days.

(21) Appl. No.: 12/857,323

(22) Filed: Aug. 16, 2010

(65) Prior Publication Data

US 2012/0041230 A1 Feb. 16, 2012

(51) Int. Cl.
*C07C 51/42* (2006.01)
*C07C 51/44* (2006.01)
*C07B 63/00* (2006.01)

(52) U.S. Cl. .............................. 562/519; 562/517
(58) Field of Classification Search .................. None
See application file for complete search history.

(56) References Cited

U.S. PATENT DOCUMENTS

| | | |
|---|---|---|
| 2,026,908 A | 1/1936 | Muth et al. |
| 3,769,177 A | 10/1973 | Eubanks et al. |
| 3,769,329 A | 10/1973 | Paulik et al. |
| 4,615,806 A | 10/1986 | Hilton et al. |
| 4,894,477 A | 1/1990 | Scates et al. |
| 4,994,608 A | 2/1991 | Torrence et al. |
| 5,001,259 A | 3/1991 | Smith et al. |
| 5,026,908 A | 6/1991 | Smith et al. |
| 5,144,068 A | 9/1992 | Smith et al. |
| 5,696,284 A | 12/1997 | Baker et al. |
| 5,731,252 A | 3/1998 | Warner et al. |
| 5,877,347 A | 3/1999 | Ditzel et al. |
| 5,877,348 A | 3/1999 | Ditzel et al. |
| 5,883,295 A | 3/1999 | Sunley et al. |
| 5,916,422 A | 6/1999 | Kimura et al. |
| 5,932,764 A | 8/1999 | Morris et al. |
| 5,942,460 A | 8/1999 | Garland et al. |
| 6,143,930 A | 11/2000 | Singh et al. |
| 6,225,498 B1 | 5/2001 | Blay et al. |
| 6,339,171 B1 | 1/2002 | Singh et al. |
| 6,627,770 B1 | 9/2003 | Cheung et al. |
| 6,657,078 B2 | 12/2003 | Scates et al. |
| 7,005,541 B2 | 2/2006 | Cheung et al. |
| 7,223,886 B2 | 5/2007 | Scates et al. |
| 2005/0197513 A1 | 9/2005 | Trueba et al. |
| 2006/0178528 A1 | 8/2006 | Cawood et al. |
| 2006/0247466 A1 | 11/2006 | Zinobile et al. |
| 2006/0293537 A1 | 12/2006 | Trueba et al. |
| 2008/0287706 A1 | 11/2008 | Powell et al. |
| 2008/0293966 A1 | 11/2008 | Scates et al. |

(Continued)

FOREIGN PATENT DOCUMENTS

| | | |
|---|---|---|
| EP | 0849248 | 6/1998 |
| WO | WO 2009/042078 | 4/2009 |

OTHER PUBLICATIONS

Jones, J.H., et al., "The Cativa Process for the Manufacture of Acetic Acid", Platinum Metals Review, 44 (3):94-105, 2000.

(Continued)

*Primary Examiner* — Yevegeny Valenrod

(57) ABSTRACT

The present invention is directed to a method of heating a light ends column through directing one or more vapor side streams from a drying column to the light ends column. The present invention is also directed to a carbonylation process for producing acetic acid, wherein one or more vapor streams from a drying column provide the external energy required to drive separation in the light ends column.

19 Claims, 1 Drawing Sheet

U.S. PATENT DOCUMENTS

2009/0088587 A1  4/2009  Powell
2009/0107833 A1  4/2009  Warner
2009/0270651 A1  10/2009 Zinobile et al.

OTHER PUBLICATIONS

M.J. Howard, et al., "C1 to acetyls: catalysis and process", Catalysis Today, Jan. 1, 1993, pp. 325-354.

International Search Report and Written Opinion for PCT/US2011/047375 mailed Feb. 9, 2012 (17 pages).
Written Opinion for PCT/US2011/047375 mailed Sep. 11, 2012.
Agrawal, "Thermally coupled distillation with reduced number of intercolumn vapor transfers", AICHE Journal, Nov. 2000, vol. 46, No. 11, pp. 2198-2210.
Castro, et al., "Esterification of fatty acids in a thermally coupled reactive distillation column by the two-step supercritical methanol method", Engineering Research and Design, 89 (2011), pp. 480-490.

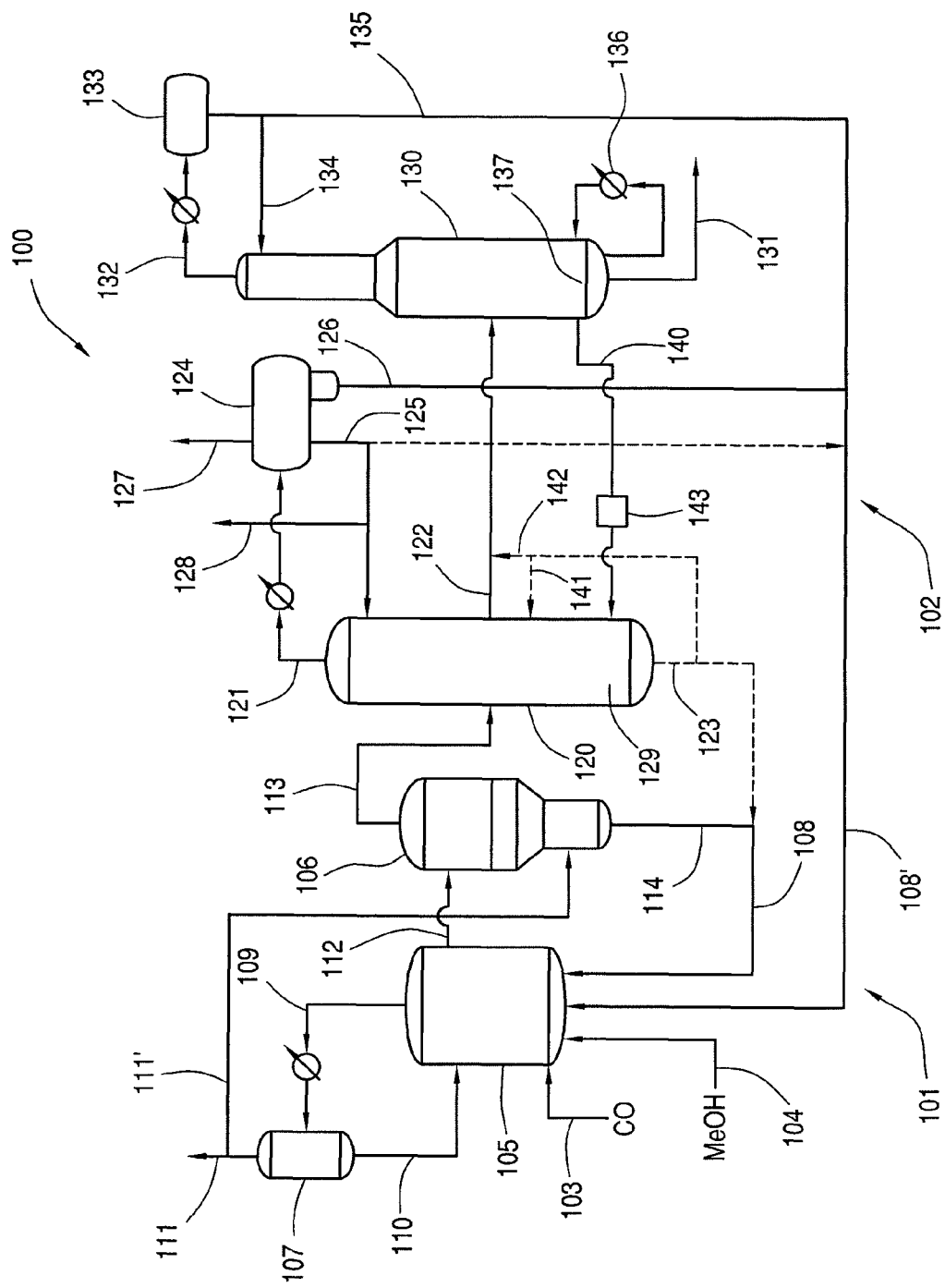

PROCESS AND SYSTEM FOR SUPPLYING VAPOR FROM DRYING COLUMN TO LIGHT ENDS COLUMN

FIELD OF THE INVENTION

The present invention is directed to a method of heating a light ends column through directing one or more vapor side streams from a drying column to the light ends column. The present invention is also directed to a carbonylation process for producing acetic acid, wherein one or more vapor streams from a drying column provide the energy required to drive the separation in the light ends column.

BACKGROUND OF THE INVENTION

A widely used and successful commercial process for synthesizing acetic acid involves the catalyzed carbonylation of methanol with carbon monoxide. The catalyst contains rhodium and/or iridium and a halogen promoter, typically methyl iodide. The reaction is conducted by continuously bubbling carbon monoxide through a liquid reaction medium in which the catalyst is dissolved. The reaction medium comprises acetic acid, methyl acetate, water, methyl iodide and the catalyst. Conventional commercial processes for carbonylation of methanol include those described in U.S. Pat. Nos. 3,769,329, 5,001,259, 5,026,908, and 5,144,068, the entire contents and disclosures of which are hereby incorporated by reference. Another conventional methanol carbonylation process includes the Cativa™ process, that is discussed in Jones, J. H. (2002), "*The Cativa™ Process for the Manufacture of Acetic Acid*," Platinum Metals Review, 44(3): 94-105, the entire content and disclosure of which is hereby incorporated by reference.

The crude acetic acid product from the reactor is processed in a purification section to remove impurities and recover acetic acid. These impurities, that may be present in trace amount, affect the quality of acetic acid, especially as the impurities are circulated through the reaction process, which, among other things, can result in the build up over time of these impurities. Conventional purification techniques to remove these impurities include treating the acetic acid product streams with oxidizers, ozone, water, methanol, activated-carbon, amines, and the like. The treatments may also be combined with the distillation of the crude acetic acid product. Generally, in many chemical processes such as acetic acid production, distillation columns consume a significant amount of energy. The distillation columns may each independently receive the energy necessary to drive the separation within the column. The present invention provides new and improved processes to advantageously increase the overall efficiency of an acetic acid production process by providing the energy required to drive separation in a separation system, preferably a light ends column, from another location within the system.

BRIEF SUMMARY OF THE INVENTION

The present invention is directed to advantageously increasing the overall efficiency of an acetic acid production process by providing the energy required to drive separation in a separation system, preferably a light ends column, from another location within the system. It has now been discovered that energy in a dying column can be advantageously controlled and transferred to other portions of the separation system, in particular, a light ends column. For example, in a first embodiment, the present invention is directed to a carbonylation method of producing acetic acid, comprising the steps of purifying a crude product stream in the light ends column to generate a product stream, directing the product stream to a drying column to generate a dried product stream and one or more vapor side streams, wherein the one or more vapor side streams provide energy to one or more separation systems.

In a second embodiment, the present invention is directed to a method of heating a light ends column comprising the steps of reacting carbon monoxide with at least one reactant in a first reactor containing a reaction medium to produce the crude product stream comprising acetic acid, wherein the at least one reactant is selected from the group consisting of methanol, methyl acetate, methyl formate, dimethyl ether and mixtures thereof, and wherein the reaction medium comprises water, acetic acid, methyl iodide, methyl acetate, and a catalyst, purifying a crude product stream in the light ends column to generate a product stream, directing the product stream to a drying column to generate a dried product stream and one or more vapor side streams, and directing the one or more vapor side streams to the light ends column, wherein the one or more vapor side streams heat the crude product stream in the light ends column. In some embodiments, a reboiler is not connected to a bottom portion of the light ends column. In some embodiments the drying column is connected to a reboiler.

In a third embodiment, the present invention is directed to a carbonylation process of producing acetic acid, comprising the steps of purifying a crude product stream in a light ends column to remove methyl iodide and methyl acetate and generate a product stream, the product stream having a lower concentration of methyl iodide and methyl acetate than the crude product stream, and drawing the product stream from a sidedraw of the light ends column, directing the product stream to a drying column to generate a dried product stream and one or more vapor side streams, wherein the one or more vapor streams from the drying column heat the crude product stream in the light end column.

In a fourth embodiment, the present invention is directed to a method of heating a light ends column comprising the steps of purifying a crude product stream in the light ends column to generate a product stream, directing the purified product stream to a drying column to generate a dried product stream, and transferring heat from the drying column to the light ends column. In some embodiments, the step of transferring heat further comprises drawing one or more vapor side streams from the drying column, and directing the one or more vapor side streams to the light ends column.

BRIEF DESCRIPTION OF THE DRAWINGS

The present invention will be better understood in view of the appended non-limiting figures, wherein:

FIG. 1 illustrates an exemplary scheme according to one embodiment of the present invention.

DETAILED DESCRIPTION OF THE INVENTION

The present invention generally relates to supplying at least some of the energy requirements of a portion of a separation system in an acetic acid production process with one or more vapor streams derived from a drying column. In a preferred embodiment, the one or more vapor side streams are directed to a light ends column, and provide the energy required to drive separation therein. In other words, some embodiments of the present invention involve transferring heat, preferably excess heat, from the drying column to drive separation in the light ends column. In conventional systems, a portion of the energy required to drive the separation in the light ends column is provided by the crude acetic acid product fed to the column. The crude acetic acid product is typically in the vapor phase. For conventional systems, in addition to the energy provided from the crude acetic acid product, the light ends column may also receive energy from a discrete reboiler at the base of the light ends column.

The present invention advantageously improves the efficiency of the acetic acid production by eliminating the need for the reboiler and using the energy in one or more vapor streams from the drying column to drive the separation of the light ends column. In preferred embodiments, the one or more vapor streams are obtained from a drying column and more preferably from the base of the drying column. Each of the one or more vapor streams may comprise acetic acid and water. The one or more vapor streams are fed directly into the light ends column, similar to the crude acetic acid product that is fed to the light ends column.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, that will vary from one implementation to another, and would be a routine undertaking for those of ordinary skill in the art having the benefit of this disclosure.

The present invention may be appreciated in connection with, for example, the carbonylation of methanol with carbon monoxide in a homogeneous catalytic reaction system comprising a reaction solvent, methanol and/or reactive derivatives thereof, a Group VIII catalyst, at least a finite concentration of water, and optionally an iodide salt.

Suitable Group VIII catalysts include rhodium and/or iridium catalysts. When a rhodium catalyst is utilized, the rhodium catalyst may be added in any suitable form such that rhodium is in the catalyst solution as an equilibrium mixture including $[Rh(CO)_2I_2]^-$ anion as is well known in the art. Optionally, the catalyst can be a rhodium diiodide dicarbonyl anion that is ionically bound to a suitable resin, e.g., polyvinylpyridine. Iodide salts optionally maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide to generate the corresponding co-promoter iodide salt stabilizer. For additional detail regarding rhodium catalysis and iodide salt generation, see U.S. Pat. Nos. 5,001,259; 5,026,908; and 5,144,068, the entireties of which are hereby incorporated by reference.

When an iridium catalyst is utilized, the iridium catalyst may comprise any iridium-containing compound that is soluble in the liquid reaction composition. The iridium catalyst may be added to the liquid reaction composition for the carbonylation reaction in any suitable form that dissolves in the liquid reaction composition or is convertible to a soluble form. Examples of suitable iridium-containing compounds that may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H+$, $[Ir(CO)_2I_4]^-H^+$, $[Ir(CH_3)I_3(CO)_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 wppm. The carbonylation of methanol utilizing iridium catalyst is well known and is generally described in U.S. Pat. Nos. 5,942,460; 5,932,764; 5,883,295; 5,877,348; 5,877,347 and 5,696,284, the entireties of which are hereby incorporated by reference.

A halogen co-catalyst/promoter is generally used in combination with the Group VIII metal catalyst component. Methyl iodide is preferred as the halogen promoter. Preferably, the concentration of halogen promoter in the liquid reaction composition is in the range 1 to 50% by weight, preferably 2 to 30% by weight.

The alkyl halide promoter may be combined with a salt stabilizer/co-promoter compound, that may include salts of a metal of Group IA or Group IIA, or a quaternary ammonium or phosphonium salt. Particularly preferred are iodide or acetate salts, e.g., lithium iodide or lithium acetate.

Other promoters and co-promoters may be used as part of the catalytic system of the present invention as described in European Patent Publication EP 0 849 248, the entirety of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 wppm.

In one embodiment, the temperature of the carbonylation reaction in first reactor 105 is preferably from 150° C. to 250° C., e.g., from 155° C. to 235° C., or from 160° C. to 220° C. The pressure of the carbonylation reaction is preferably from 10 to 200 bar, preferably 10 to 100 bar, most preferably 15 to 50 Bar. Acetic acid is typically manufactured in a liquid phase reaction at a temperature of from about 160-220° C. and a total pressure of from about 20 to about 50 bar.

FIG. 1 shows an exemplary carbonylation system 100 for the production of acetic acid in accordance with embodiments of the present invention. Other carbonylation systems that may be used with embodiments of the present invention include those described in U.S. Pat. Nos. 7,223,886, 7,005, 541, 6,6657,078, 6,339,171, 5,731,252, 5,144,068, 5,026,908, 5,001,259, 4,994,608, and U.S. Pub. No. 2008/0287706, 2008/0293966, 2009/0107833, 2009/0270651, the entire contents and disclosures of which are hereby incorporated by reference. System 100 comprises a carbonylation section 101 and a purification section 102. It should be understood that the carbonylation section 101 shown in FIG. 1 is exemplary and other components may be used within the scope of the present invention.

The carbonylation section 101 comprises carbon monoxide feed stream 103, reactant feed stream 104, reactor 105, flasher 106 and recovery unit 107. Preferably the carbon monoxide and at least one reactant are continuously fed by feed streams 103 and 104, respectively, to reactor 105. The reactant feed stream 104 may supply at least one reactant selected from the group consisting of methanol, methyl acetate, methyl formate, dimethyl ether, and/or mixtures thereof, to the reactor 105. In preferred embodiments, the reactant feed stream 104 may supply methanol and/or methyl acetate. Optionally, the reactant feed stream 104 may be connected to one or more vessels (not shown) that store fresh reactants for the carbonylation process. In addition, although not shown there may be a methyl iodide storage vessel and/or catalyst vessel connected to the reactor 105 for supplying fresh methyl iodide and catalyst as needed to maintain reaction conditions.

One or more recycle feed streams 108, 108' preferably from the purification section, may be fed to reactor 105. Although two recycle feed streams 108, 108' are shown in FIG. 1, there may be multiple streams that are fed separately to reactor 105. As discussed below, the recycle feed streams 108 may comprise the components of the reaction medium, as well as residual and/or entrained catalyst and acetic acid.

Optionally, there may be at least one fresh water stream (not shown) that may be fed to reactor 105.

In preferred embodiments, reactor 105 is a liquid phase carbonylation reactor. The reactor 105 is preferably either a stirred vessel or bubble-column type vessel, with or without an agitator, within which the reacting liquid contents are maintained, preferably automatically, at a predetermined level, that preferably remains substantially constant during normal operation. Fresh methanol from feed stream 104, carbon monoxide from feed stream 103, and recycle streams 108, along with optional methyl iodide streams, catalyst streams, and/or water streams, are continuously introduced into reactor 105 as needed to maintain at least a water concentration of from 0.1 wt % to 14 wt. % in the reaction medium.

In a typical carbonylation process, carbon monoxide is continuously introduced into the carbonylation reactor, preferably via a distributor, and desirably below the agitator, that may be used to stir the contents. The gaseous feed preferably is thoroughly dispersed through the reacting liquid by this stirring means. A gaseous/vapor purge stream 109 desirably is vented from the reactor 105 to prevent buildup of gaseous by-products, inerts, and to maintain a set carbon monoxide partial pressure at a given total reactor pressure. The temperature of the reactor may be controlled and the carbon monoxide feed is introduced at a rate sufficient to maintain the desired total reactor pressure. Gaseous purge stream 109 may be scrubbed with acetic acid and/or methanol in recovery unit 107 to recover low boiling components, such as methyl iodide. The gaseous purge stream 109 may be condensed and fed to a recovery unit 107 that may return low boiling components 110 to the top of reactor 105. The low boiling components 110 may comprise methyl acetate and/or methyl iodide. Carbon monoxide in the gaseous purge stream 109 may be purged in line 111 or fed via line 111' to base of flasher 106 to enhance rhodium stability.

Carbonylation product is drawn off from the carbonylation reactor 105 at a rate sufficient to maintain a constant level therein and is provided to a flasher 106 via stream 112. In flasher 106, the carbonylation product is separated in a flash separation step with or without the addition of heat to obtain a crude product stream 113 comprising acetic acid, and a catalyst recycle stream 114, comprising a catalyst-containing solution that preferably is recycled to the reactor via stream 108. The catalyst-containing solution predominantly contains acetic acid, the rhodium catalyst, and the iodide salt, along with lesser quantities of methyl acetate, methyl iodide, and water, as discussed above. The crude product stream 113 comprises acetic acid, methyl acetate, methyl iodide, water, alkanes, and permanganate reducing compounds (PRC's). PRC's, may include, for example, compounds such as acetaldehyde, acetone, methyl ethyl ketone, butyraldehyde, crotonaldehyde, 2-ethyl crotonaldehyde, 2-ethyl butyraldehyde and the like, and the aldol condensation products thereof. Dissolved gases exiting the reactor 105 and entering the flasher 106 comprise a portion of the carbon monoxide and may also contain gaseous by-products such as methane, hydrogen, and carbon dioxide, and inerts such as nitrogen and argon, and oxygen. Such dissolved gases exit the flasher 106 as part of the crude product stream 113. The crude product stream 113 from flasher 106 is directed to purification section 102.

In one embodiment, purification section 102 comprises a light ends column 120 and a drying column 130. In further embodiments, the purification section 102 may comprise one or more columns for removal of PRC's, guard beds, vent scrubbers, and/or heavy ends columns. The PRC removal columns are described in U.S. Pat. Nos. 6,143,930, 6,339,171, and 7,223,886, and U.S. Publication Nos. 2005/0197513, 2006/0247466, and 2006/0293537, the entire contents and disclosures of which are hereby incorporated by reference. Guard beds are described in U.S. Pat. Nos. 4,615,806, 4,894,477, and 6,225,498, the entire contents and disclosures of which are hereby incorporated by reference.

The crude product stream 113 from the carbonylation section 101 is fed to the light ends column 120 to obtain a low-boiling overhead vapor stream 121, a product side stream 122, and an optional bottoms stream 123. The temperature at the base of the light ends column 120, i.e., temperature of the optional exiting bottoms stream 123, preferably is from 120° C. to 170° C. In addition, the temperature at the top of the light ends column, i.e., temperature of the low-boiling overhead vapor stream 121, preferably is from 100° C. to 145° C.

The low-boiling overhead vapor stream 121 may comprise methyl iodide, methyl acetate, water, PRC's, acetic acid, alkanes, and dissolved gases. As shown, low-boiling overhead vapor stream 121 preferably is condensed and directed to an overhead phase separation unit, as shown by overhead receiver or decanter 124. Conditions are desirably maintained such that low-boiling overhead vapor stream 121, once in decanter 124, will separate into a light phase 125 and a heavy phase 126. Non-condensable gases may be removed by vent stream 127 and optionally fed to one or more scrubbers (not shown) to recover any low boiling point components.

Light phase 125 preferably comprises water, acetic acid, and PRC's, as well as methyl iodide and methyl acetate. As shown in FIG. 1, light phase 125 may be refluxed to light ends column 120. A portion of the light phase 125 may also be separated and processed in one or more columns (not shown) to remove PRC's via line 128. Optionally, a portion of the light phase 125 may also be returned to carbonylation section 101 and co-fed with recycle stream 108' to reactor 105. The heavy phase 126 from the decanter 124 can be conveniently recirculated, either directly or indirectly, to the reactor 105 via recycle stream 108'. For example, a portion of the heavy phase 126 may be recirculated to the reactor 105, with a slip stream (not shown), generally a small amount, e.g., from 5 to 40 vol. %, or from 5 to 20 vol. %, of the heavy phase 126 being directed to the one or more columns to remove PRC's.

Product side stream 122 from the light ends column may comprise acetic acid and water. In one embodiment, product side stream 122 may comprise at least 70 wt. % acetic acid, e.g., at least 80 wt. % or at least 85 wt. %, and may comprise less than 15 wt. % water, e.g., less than 10 wt. % or less than 5 wt. %. In terms of ranges, product stream 122 comprises from 0.01 wt. % to 20 wt. %, 0.1 wt. % to 10 wt. %, or 1 wt. % to 5 wt. % water. Product side stream 122 preferably is in the liquid phase and is withdrawn from the light ends column 120 at a temperature of from 115° C. to 160° C., e.g., from 125° C. to 155° C. Product side stream 122 may be fed to the drying column 130 to obtain a dried product stream 131 and an overhead stream 132 comprised primarily of separated water. The dried purified product stream 131 preferably comprises acetic acid in an amount greater than 90 wt. %, e.g., greater than 95 wt. % or greater than 98 wt. %. Optionally, the dried purified product stream 131 may be further treated in one or more guard beds (not shown) and/or heavy end columns (not shown) to further remove impurities. The overhead stream 132 of the drying column may be condensed and separated in a receiver 133. A portion of the liquid from receiver 133 may be refluxed to drying column 130 via line 134 and another portion may be returned to the carbonylation section 101 via line 135. The temperature at the base of the drying column 130, i.e., temperature of the exiting dried purified product stream 131, preferably is from 130° C. to 185° C. In addition, the temperature at the top of the drying column 130, i.e., temperature of the overhead stream 132, preferably is from 110° C. to 150° C.

The external energy introduced (such as energy from a reboiler heat exchange or direct injection) to separate the components of the product side stream 122 in drying column 130 is generally larger than the external energy required for light ends column 120. In one embodiment, the reboiler 136 of drying column 130 provides substantially the same amount of energy under normal or partial conditions, and thus may result in an excess of latent energy that may be used as an external source of energy to drive separation in the light ends column 120. As shown in FIG. 1, a reboiler 136 may be used to supply the energy requirements for the drying column 130. A portion of the dried purified product stream 131 may be re-circulated to the drying column 130 by reboiler 136.

Returning to the light ends column 120, since the optional light ends bottoms stream 123 typically will comprise heavy components, acetic acid, water, and entrained catalyst, it may be beneficial to recycle all or a portion of the light ends bottoms stream 123 to reactor 105 via one or more recycle streams 108. The light ends bottoms stream 123 may be combined with the catalyst recycle stream 114 from flasher 106 and returned together to reactor 105, as shown in FIG. 1. Optionally, the light ends bottoms stream 123 may be fed to the base of the flasher 106.

In a conventional system, the energy to drive separation in the light ends column may be supplied by the heat of the crude product stream and/or a reboiler. The crude product stream 113 exits flasher 106 at a temperature of from 115° C. to 170° C., e.g., from 125° C. to 165° C. or 130° C. to 160° C. In one exemplary embodiment, the energy needed to drive separation in the light ends column is at least 6,000,000 BTU/hr, e.g., at least 10,000,000 BTU/hr, or at least 15,000,000 BTU/hr.

When operating under steady state conditions or in normal operations, the crude product stream 113 generally provides sufficient energy to drive the separation in the light ends column 120. However, outside of normal operations or partial operating conditions, such as in a start up or reactor shutdown mode, the crude product stream 113 may not provide sufficient energy alone to drive the separation in the light ends column. Under those conditions, a separate reboiler is conventionally required to supply energy to the base of the light ends column to drive the separation. Even under normal conditions it may be necessary to supply additional energy to the light ends column beyond the capacity of the crude product stream.

During the production of acetic acid, the process preferably operates continuously under normal steady state conditions. However, due to start up, reactor shutdown, reactor rate reductions, trips, or distillation train upsets, the production distillation process may operate under partial conditions. When operating under these partial conditions and outside of normal operation, the energy required to drive the separation in the light ends column needs a source other than the crude product stream 113. Embodiments of the present invention advantageously provide the energy to drive the separation in the light ends column 120 using one or more vapor streams 140 from the drying column 130. Preferably, the one or more vapor streams 140 allow the light ends column to operate under normal and partial conditions. More preferably the one or more vapor streams 140 allow the light ends column to operate without the need for a dedicated reboiler.

During normal operation, the one or more vapor side streams 140 may provide a minor portion of the energy needed to drive separation in the light ends column, i.e., less than 50% of the total required energy. In terms of ranges, the one or more vapor side streams 140 may provide from 1% to 50%, e.g., from 1% to 25% of the total required energy. The light ends column may use both the energy from the crude product stream 113 and the one or more vapor side streams 140. In one embodiment, when the energy from the flasher 106 is insufficient to drive the separation in the light ends column 120, the one or more vapor side streams 140 may provide the energy from the excess latent energy of the drying column 130.

During partial operation, the one or more vapor side streams 140 may provide a majority of the energy needed to drive separation in the light ends column. Under certain conditions when little to no crude product stream 113 is provided to the light ends column, the one or more vapor side streams 140 may provide all of the energy required to drive separation in the light ends column. In one preferred embodiment, under partial operation, the one or more vapor side streams 140 may provide from 1% to 100%, e.g. from 10% to 85%, of the total energy required to drive separation in the light ends column. The one or more vapor side streams 140 preferably provide all of the energy or at least 20% of the total energy required by the light ends columns, e.g., at least 50% or at least 70%. In some embodiments, such as during reactor shutdown operation, the one or more vapor side streams 140 may provide 90% to 100% of the total energy required to drive separation in the light ends column. Also, during distillation system start up, the one or more vapor side streams 140 may provide 1% to 100% of the total energy required to drive separation in the light ends column. In some embodiments, for example, during an initial reactor startup operation, the one or more vapor side streams 140 may provide 50% to 100% of the energy required to drive separation in the light ends column. In some embodiments, during a reactor startup operation, the one or more vapor side streams 140 may provide 1% to 50% of the energy required to drive separation in the light ends column. In other embodiments, when the reactor feed rate is reduced by 50% or less from normal operating conditions, the drying column 130 may supply from 1 to 60% of the energy for the light ends column 120. In a reactor trip, providing external energy from the drying column 130 allows the distillation system to be maintained at stable, steady conditions so that the reactor may restart and resume producing acetic acid product at normal operation rate more quickly.

In one embodiment, the drying column may have excess latent energy and the one or more vapor side streams 140 may transfer the excess and/or latent energy. Excess energy or latent energy refers to energy provided to the drying column from a reboiler, that is not used to drive separation in the drying column, and may vary depending on the conditions of the process. In one embodiment, at least 3% of the latent energy from the drying column may be transferred, e.g., at least 20% or least 45%. In preferred embodiments, the one or more vapor streams 140 may transfer all of the excess latent energy from the drying column.

The one or more vapor side streams 140 are drawn from a lower portion 137 of the drying column 130, and are directed to a lower portion 129 of the light ends column 120. Lower portion 137 of the drying column is preferably drawn at a point below where purified product stream 122 is fed to drying column 130. In one embodiment, the one or more vapor streams are withdrawn from a base section of the drying column in the vapor vicinity proximate to where the returns from reboiler 136 are fed to drying column. When the one or more vapor side streams 140 are directed to the lower portion 129 of the light ends column 120, the one or more vapor side streams are fed into the light ends column 120 at a point below where the product side stream 122 is drawn off. In some embodiments, light ends column 120 comprises a number of trays layered throughout the length of the column (not shown). In some embodiments, the one or more vapor side streams are fed into the light ends column 120 at a point below the first tray (or first packed section) from the base. In some embodiments, the one or more vapor side streams are fed into the light ends column 120 at a point below the tenth tray from the base. In some embodiments, the one or more vapor side streams are fed into the light ends column 120 at a point below where stream 122 exits the light ends column.

The one or more vapor side streams 140 comprise acetic acid and water. In some embodiments, the one or more vapor side streams 140 comprise a major portion of acetic acid and a minor portion of water. In terms of ranges the one or more vapor side streams 140 comprise from 90 wt. % to 99.9 wt. % acetic acid, e.g., from 95 wt. % to 99.95 wt. %, and from 0.01 wt. % to 10 wt. % water, e.g., from 0.05 wt. % to 1 wt. %. It is preferred that the composition of the one or more vapor side streams 140 has a lower water content than the product side stream 122 fed from the light ends column 120 to the drying column 130. The one or more vapor side streams preferably have a temperature of from 130° C. to 185° C., e.g., 130° C. to 180° C., 150° C. to 180° C., 155° C. to 180° C., or 160° C. to 175° C., and may have a pressure of from 2.5 atm to 5 atm, e.g., 3 atm to 4.5 atm. In one embodiment, it is preferred that the one or more vapor side streams 140 have a temperature that is higher, e.g., at least 5° C., 10° C., 20° C., or 30° C., than the crude acetic acid product 113. In another embodiment, it is preferred that the one or more vapor side streams 140 have a temperature that is higher than the product side stream 122.

The acetic acid that is fed in the one or more vapor streams is preferably separated in the light ends column 120 and returns to the drying column 130 and is eventually withdrawn as dried purified product stream 131. In preferred embodiments, when column 130 is not in internal reflux mode no dried purified product stream 131, the acetic acid that is directed to the one or more vapor streams is a smaller amount as compared to the acetic acid vaporized in base area 137 of drying column 130.

In some embodiments, a portion of the light ends bottoms stream 123 may be directed to other parts of the system, depending on the operating conditions of the system. For example, during reactor shut down operation, a portion of the light ends bottoms stream 123 may be introduced to the light ends column 120 via return line 141. Return line 141 preferably enters the light ends column 120 at a point where the product side stream 122 is withdrawn or below that point. In some embodiments, a portion of the side stream 122 may be returned to the light ends column 120. As indicated above, the one or more vapor streams 140 have a majority portion of acetic acid. As a result, the acetic acid concentration in the bottoms stream 123 would be expected to increase the amount of acetic acid returned to the reactor 105. To promote the return of the acetic acid to the drying column 130, return 141 introduces a portion of the acetic acid-enriched bottoms stream 123 further up the light ends column 120.

In conventional processes, a portion of the product stream 122 may be portioned and returned to the light ends column 120 at a lower tray. This is called a reflux stream to the lower section of light ends column 120 and provides a scrub to lower section for removal of entrained catalyst, usually in the wppm levels. In addition, the reflux stream provides a working base inventory in the lower section 129 of the light ends column 120. In embodiments of the present invention, using a portion of stream 123 for this purpose via line 141, may reduce and/or eliminate the need for a reflux stream from product stream 122. Advantageously, embodiments of the present invention may allow a higher net percentage of stream 122 to be sent to drying column 130. Stream 141 may reduce by a marginal amount the rectification load for light ends column 120.

In other embodiments, a portion of the light ends bottoms stream 123 may be directed to the drying column 130 via line 142. Line 142 may be co-fed with side stream 122 or optionally separately fed to drying column 130. For example, during drying column total recycle operation, the portion of the light ends bottoms stream 123 in line 142 may provide direct recycle to maintain the drying column 130 base liquid inventory.

In some embodiments, a method of the present invention further comprises regulating one or more of the vapor side streams 140. Regulation of the one or more vapor side streams 140 may be achieved by one or more valves 143. In some embodiments, the one or more valves comprises a manual check type valve, flow control type valve, positive isolation type valve, and combinations thereof. While not being bound to one particular theory, the presence of one or more valves provides the ability to control the base temperature in the light ends column and/or inhibits cross contamination/backflow into the drying column. In some embodiments, the one or more valves 143 provide the ability to regulate a one-way flow of the one or more vapor side streams 140 into the lower vapor portion 129 of the light ends column 120. Advantageously, the one or more valves 143 inhibit the back flow of any of the material at the base of the light ends column 120 from entering the drying column 130.

In order that the invention disclosed herein may be more efficiently understood, a non-limiting examples are provided below. The following examples describe various embodiments of the inventive methods.

EXAMPLES

Using an ASPEN Radfrac™ computer model, the process shown in section 102 of FIG. 1 was simulated under normal operating conditions. For normal operating conditions, the light ends column receives heat from one or more vapor streams from the drying column without need to receive any heat from a dedicated reboiler (within Radfrac modeling capability) attached at the base of the light ends column.

Example 1

At design production rate for an acetic acid production, the reboiler of the drying column provides sufficient energy to the drying column to drive the separation without excess energy. The energy required to drive separation in the light ends column is provided by energy from the flasher.

Example 2

When the production rates of Example 1 are reduced by half, the energy from the flasher provides approximately 90% of the total energy required to drive separation in the light ends column. The light ends column requires approximately an additional 10% of energy. The drying column has approximately 38% relative excess energy available. One or more vapor side streams transfer a portion of the excess energy from the drying column to the light ends column and provide the additional approximately 10% of energy required to drive separation in the light ends column.

Example 3

When the production rates of Example 1 are a quarter, the energy from the flasher provides approximately 25% of the total energy required to drive separation in the light ends column. The light ends column requires approximately an additional 75% of energy. The drying column has approximately 49% relative excess energy available, and one or more vapor side streams transfer a portion of the excess energy from the drying column to the light ends column and provide the additional approximately 75% of energy required to drive separation in the light ends column.

Example 4

During a partial condition when the reactor trips and the purification section remains operating, no energy is provided from the flasher to the light ends column. The drying column has approximately 49% relative excess energy available, and one or more vapor side streams transfer a portion of the excess energy from the drying column and provide the energy required to drive separation in the light ends column.

Example 5

During a partial condition when the purification section starts up before the reactor starts up, no energy is provided from the flasher to the light ends column. The drying column has approximately 49% relative excess energy available, and one or more vapor side streams transfer a portion of the excess energy from the drying column to provide the energy required to drive separation in the light ends column. The total energy required under these conditions may be less than the energy required under the partial conditions described in Example 4. Changing the reactor operating rate in Example 4 would be expected to also change the total energy required for the light ends column.

Example 6

During a partial condition when the reactor and purification sections are starting up, the energy from the flasher provides approximately 25% of the total energy required to drive separation in the light ends column. Similar to Example 3, the light ends column requires approximately an additional 75% of the total energy. The drying column has approximately 49% relative excess energy available, and one or more vapor side streams transfer a portion of the excess energy to provide the energy required to drive separation in the light ends column.

Example 7

During a partial condition as the reactor and purification sections continue to transition to the operating rates of Example 1, the energy from the flasher provides approximately 85% of the total energy required to the drive separation in the light ends column. The light ends column requires approximately an additional 15% of energy. The drying column has approximately 49% relative excess energy available, and one or more vapor side streams transfer a portion of the excess energy from the drying column to provide the required energy to drive separation in the light ends column.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments that refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A carbonylation method of producing acetic acid, comprising the steps of:
    purifying a crude product stream in a light ends column to generate a product stream;
    directing the product stream to a drying column to generate a dried product stream and one or more vapor side streams,
    wherein the one or more vapor side streams provide energy to one or more separation systems.

2. The method according to claim 1, further comprising directing the one or more vapor side streams to the light ends column.

3. The method according to claim 2, wherein the one or more vapor side streams are drawn from a lower portion of the drying column.

4. The method according to claim 2, wherein the one or more vapor side streams are fed to a base of the light ends column.

5. The method according to claim 2, wherein a reboiler is not connected to a bottom portion of the light ends column.

6. The method according to claim 1, wherein the one or more vapor side streams heat the crude product stream in the light ends column.

7. The method according to claim 1, wherein the drying column is connected to a reboiler.

8. The method according to claim 1, wherein the one or more vapor side streams comprise acetic acid and water.

9. The method according to claim 8, wherein the one or more vapor side streams comprise acetic acid in an amount of from 90 wt. % to 99.9 wt. %.

10. The method according to claim 8, wherein the one or more vapor side streams comprise water in an amount of from 0.01 wt. % to 10 wt. % water.

11. The method according to claim 1, wherein the one or more vapor side streams have a temperature of from 130° C. to 185° C.

12. The method according to claim 1, wherein the one or more vapor side streams are fed to a base of the light ends column.

13. The method according to claim 1, wherein the light ends column operates within a base temperature of from 120° C. to 170° C.

14. The method according to claim 1, wherein from 1% to 50% of a total amount of energy required to drive separation in the light ends column is provided by the one or more vapor side streams.

15. The method according to claim 1, wherein from 50% to 100% of a total amount of energy required to drive separation in the light ends column is provided by the one or more vapor side streams.

16. A method according to claim 1, further comprising the step of:
reacting carbon monoxide with at least one reactant in a first reactor containing a reaction medium to produce the crude product stream comprising acetic acid,
wherein the at least one reactant is selected from the group consisting of methanol, methyl acetate, methyl formate, dimethyl ether and mixtures thereof, and
wherein the reaction medium comprises water, acetic acid, methyl iodide, methyl acetate and a catalyst.

17. A carbonylation method of producing acetic acid, comprising the steps of:
purifying a crude product stream in a light ends column to remove methyl iodide and methyl acetate and generate a product stream, the product stream having a lower concentration of methyl iodide and methyl acetate than the crude product stream, and
drawing the product stream from a sidedraw of the light ends column;
directing the product stream to a drying column to generate a dried product stream and one or more vapor side streams;
wherein the one or more vapor streams from the drying column heat the crude product stream in the light end column.

18. The method according to claim 17, wherein the one or more vapor side streams comprise acetic acid and water.

19. The method according to claim 17, wherein the one or more vapor side streams have a temperature of from 130° C. to 185° C.

* * * * *